(12) United States Patent
Engel

(10) Patent No.: US 6,716,639 B1
(45) Date of Patent: Apr. 6, 2004

(54) IMMUNOASSAY APPARATUS FOR DETECTING NICOTINE OR CONTININE

(75) Inventor: Matthias Werner Engel, Ahrensburg (DE)

(73) Assignee: ulti med Products (Deutschland) GmbH, Ahrensburg (DE)

( * ) Notice: Subject to any disclaimer, the term of this patent is extended or adjusted under 35 U.S.C. 154(b) by 0 days.

(21) Appl. No.: 09/188,332

(22) Filed: Nov. 9, 1998

(30) Foreign Application Priority Data

Nov. 17, 1997 (DE) .......................................... 197 50 869

(51) Int. Cl.⁷ ............................................ G01N 33/558
(52) U.S. Cl. ........................... 436/514; 422/55; 422/56; 422/57; 422/58; 435/287.1; 435/287.2; 435/287.7; 435/287.9; 435/805; 435/810; 435/970; 435/7.9; 436/169; 436/172; 436/518; 436/524; 436/525; 436/531; 436/533; 436/534; 436/810; 436/815
(58) Field of Search ............................... 422/55–58, 61; 435/287.1, 287.2, 287.7, 287.9, 805, 810, 970, 7.9; 436/514, 518, 524, 525, 531, 533, 534, 169, 172, 810, 815

(56) References Cited

U.S. PATENT DOCUMENTS 5,602,040 A * 2/1997 May et al. .................. 436/514

FOREIGN PATENT DOCUMENTS

WO 93/03175 * 2/1993

* cited by examiner

Primary Examiner—Christopher L. Chin
(74) Attorney, Agent, or Firm—Pillsbury Winthrop LLP

(57) ABSTRACT

The invention relates to an immunoassay apparatus, comprising a dry, porous substrate having at least two sections (1, 2), communicating with one another in the moist state by capillary action, wherein the first section (1) has a marked detection reagent for the substance to be detected and the second section (2) has an immobilized binder reagent for the substance to be detected, and wherein the reaction product comprising the substance to be detected and the marked detection reagent migrates by capillary action from the first section into the second section in the moist state, and is characterized in that the marked detection reagent is a dye-carrying reagent for nicotine or cotinine.

10 Claims, 1 Drawing Sheet

IMMUNOASSAY APPARATUS FOR DETECTING NICOTINE OR CONTININE

CROSS-REFERENCE TO RELATED APPLICATIONS

Figure 1:
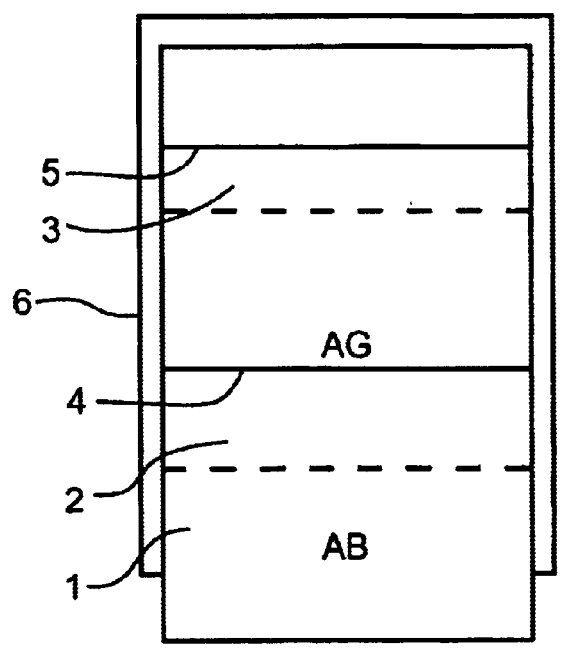

This claims priority to German Application No. 197 50 869.3, filed Nov. 17, 1997, which is incorporated in its entirety herein by reference.

The invention relates to a immunoassay apparatus for detecting nicotine or cotinine.

Nicotine is a primary alkaloid of tobacco; the nicotine content in commercial tobaccos can amount to between 0.3 and 3%, and in heavy grades, up to 7%. However, nicotine is broken down relatively quickly in the body; the primary metabolite of nicotine is cotinine, which is the 2-pyrrolidinone corresponding to nicotine. While nicotine has a biological half-life in human blood of approximately one-half hour, cotinine, which as a secondary alkaloid also occurs in tobacco, has a biological half-life of about 30 to 40 hours and occurs in the blood, serum or urine of smokers in substantially higher concentrations than nicotine. Detecting cotinine is therefore considered to be a reliable indicator of a person's smoking or nonsmoking.

Since in certain work environments, such as in the chemical or oil industry, smoking can present a considerable risk because of the attendant risk of fire or explosion, on the one hand, and on the other alkaloids not contained in tobacco but other accompanying products produced during smoking are also considered to have a considerable risk to health, there has long been a need, not only in the processing industry but also on the part of insurance companies, for instance, for a quickly performed and reliable test for checking whether persons who say they are nonsmokers are in fact nonsmokers. However, until now, no rests for nicotine or cotinine that could be performed quickly and simply were available.

It is indeed already known that cotinine, as a primary metabolite of nicotine, is suitable for detecting smoking with the aid of immunoassays; for instance, van Vunakis, H. et al., in Am. J. Obstet. Gynecol. 120, 64 ff. (1974) have described a radio immunoassay for detecting nicotine and cotinine in the amniotic fluid of pregnant women smokers, and Bjercke, R. J. et al., in Journal of Immunological Methods, 90 (1986) 203 pp., have described an ELISA test for detecting antibodies to nicotine and cotinine. Although radio immunoassays and ELISA tests are relatively reliable methods for detecting nicotine or cotinine, still they can be performed only by professionals and are time-consuming, and thus are completely unsuitable as a reliable, conveniently performed fast test.

Surprisingly, it has now been discovered that such a fast test for nicotine or cotinine can be performed on the basis of an immunoassay, if an immunoassay apparatus in accordance with the main claim is used.

Immunoassays are highly sensitive determination methods, which are based on the specificity of immunological reactions, primarily antigen and antibody reactions. For qualitative or quantitative analysis, it is necessary to mark one of the reaction partners with a readily detectable and measurable indicator substance, such as radioactive isotopes, enzymes, dyes and fluorescent dyes. Usually this involves solid-phase tests, in which the marker bound to the solid phase is measured. Microtiter slides, as in ELISA tests, or solid substrates, for which nitrocellulose has proven itself in particular, are used as the solid phase. Solid-phase tests are designed such that a solid substrate is subdivided into various sections, and the liquid, aqueous medium to be tested is applied to the initial part of the substrate; the liquid can then move by capillary action of the substrate all the way through the substrate, and excess liquid is rinsed off or caught in a so-called liquid trap. The solid substrate is provided with either marked antigen or marked antibody inside a first section, so that when the substance to be detected, which is in solution, is added an antigen-antibody reaction ensues; the marker can be coupled to either the antigen or the antibody. The antigen-antibody reaction product then migrates with the liquid into a second section, which has either an immobilized antigen or an immobilized antibody, with which the product of the substance to be detected and the antigen or antibody is converted in a competitive reaction, or if a sandwich test is involved, is converted twice. As a result, a concentration of the marker in this region ensues, and the concentration can then be assessed qualitatively or quantitatively with a suitable measuring instrument, or if dyes that are adsorbent in the visible range are used as markers, can be perceived with the naked eye. Excess and therefore unused marked antigens or antibodies may possibly migrate into a third section, in which they are then bound for instance by antigens or antibodies with a different specificity and thus can be used as controls.

Solid-phase immunoassays of the competitive or sandwich type are familiar to one skilled in the art and therefore need not be described in further detail. For instance, such tests are described in detail in European Patent Disclosures EP-A1 0 284 232 or EP B1 0 291 194.

The apparatus according to the invention comprises a so-called "dipstick", that is, a porous substrate in which the coupling product of the detection reagent and the substance to be detected can migrate by capillary action, and which to improve its mechanical properties is in turn secured to a substrate, such as a plastic slide. The substrate, that is, the solid-phase material, may comprise various porous materials that thus dictate capillary action, such as cellulose, polyamide, pretreated papers, and so forth, but preferably nitrocellulose is used. The substrate has a first section, which carries a marked detection reagent for the substance to be detected, which depending on the arrangement of the test is either a marked antibody or a marked antigen. The marking is done with particles, which are preferably either small, dyed plastic particles, especially of polystyrene, or metal sols, and especially gold sol, because even when greatly diluted gold sol has a bluish-red coloring that can be readily seen by the naked eye. When his first section is moistened with the substance to be detected, which is in solution, a coupling product of marked detection reagent and the compound to be analyzed is created; in the moist state of the substrate, this product can migrate out of the first section into the second section. An immobilized binder reagent, which in turn depending on the layout of the test may be a non-marked antibody or a non-marked antigen, is located in the second section.

If desired, the apparatus can also include a third section, namely a control zone, from which it can be told whether the process has proceeded correctly. The marked antigens or antibodies not used by the coupling with the binder reagent can then be converted in this control zone, for instance, with an immobilized antigen or antibody of different specificity, or the control zone may contain a substance which for instance reacts with the aqueous substrate by changing color, so that in one way or another an indication is made that the aqueous solution that was applied in the first section has in fact reached the location of the control strip, so that the reaction can then be considered to have ended.

Preferably, according to the invention the reaction is performed such that an antibody capable of migration is used in the first section and an immobilized antigen is used in the second section; by way of example, antigens and antibodies of the kind described at length in the above-cited work by Bjercke, R. J. et al. can be used. The antibodies are conjugated for use with a marker, especially with gold sol.

If a third section with a control option is desired, then in this third section by way of example a commercially available "anti-mouse" immunoglobulin from rabbits can be used, which is immobilized there if antibodies from the mouse are used in the first section.

To protect the apparatus or dipstrip against environmental factors such as moisture, dust, and so forth, the dipstrip is preferably located in a hood, which encloses the entire strip except for part of the first section. The hood preferably comprises water-repellent, dustproof plastic. In a further preferred embodiment, the hood is in at least two parts, so that the part of the test strip that protrudes out of the hood can also be covered by a removable part of the hood. The part of the test strip that has the first section and that protrudes from the hood or part of the hood is selected such that this part can be saturated with the body fluid to be tested, such as urine in particular, and the saturating fluid then migrates uniformly through the entire strip.

The invention will now be described in further detail below in conjunction with the drawings.

Figure 2:
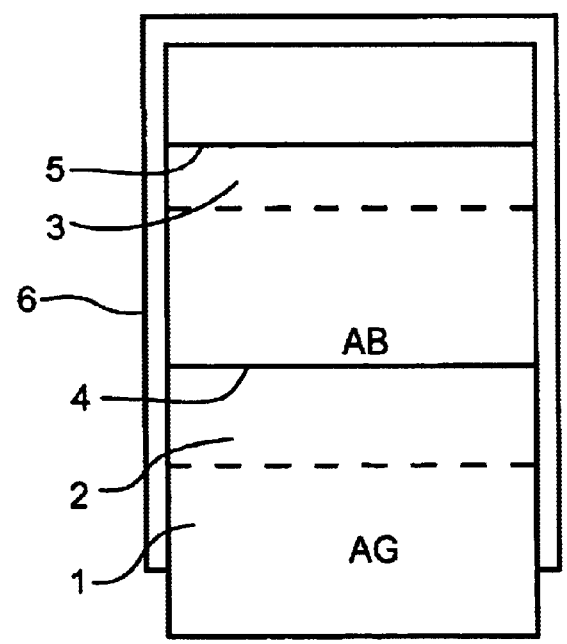

FIG. 1 schematically shows an apparatus according to the invention, in which a dye-carrying antibody is used as the marked detection reagent, and an antigen is used as the binder reagent; and FIG. 2 schematically shows the case in which the marked detection reagent is an antigen and the binder reagent is an antibody.

In a dry, porous test strip, for instance of nitrocellulose, three sections (1, 2, 3) are subdivided; aqueous liquid can migrate through them by capillary action. The overlapping boundaries between sections are represented by dashed lines.

When a marked antibody is used as the detection reagent, it migrates, after reacting with the substance to be analyzed, across the section boundary from section 1 to section 2, until the line is reached at which immobilized antigen is located as a binder reagent. This test line if marked 4. Excess detection reagent then migrates further over the boundary between a second and third section (2, 3) into the control section 3, where it meets a line of an immobilized substance to be detected of different specificity (5). Except for part of the first suction, the test strip is enclosed by a housing (6).

However, the reaction may also be performed in such a way that, as shown in FIG. 2, section 1 contains an antigen as the marked detection reagent, which after reacting with the substance to be detected migrates out of the analysis fluid across the boundary between sections 1 and 2 until it reaches an immobilized antibody on the line (4), and from there migrates on across the boundary between the sections (2, 3) until reaching a further immobilized detection reagent of different specificity (5).

I claim:

1. An immunoassay apparatus consisting of a dry, porous substrate having two sections, communicating with one another in a moist state by capillary action, wherein a first section has a marked detection reagent for nicotine and cotinine and a second section has an immobilized binder reagent for nicotine and cotinine, and wherein the reaction product comprising nicotine and cotinine and the marked detection reagent migrates by capillary action from the first section into the second section in the moist state, wherein the marked detection reagent is a dye-carrying reagent for nicotine or cotinine.

2. The immunoassay apparatus of claim 1, wherein a nicotine or cotinine antigen forms a stationary phase.

3. The immunoassay apparatus of claim 1, wherein a nicotine or cotinine antibody forms a stationary phase.

4. The immunoassay apparatus of claim 1, wherein a migrating antibody or a migrating antigen is conjugated with dyed plastic particles or metal sols.

5. The immunoassay apparatus of claim 1, wherein the apparatus is located in a hood that protects it against environmental factors.

6. The immunoassay apparatus of claim 5, wherein the hood comprises plastic.

7. The immunoassay apparatus of claim 6, wherein the plastic hood is in two parts.

8. The immunoassay apparatus of claim 4 comprising a conjugate that contains a gold sol.

9. An immunoassay apparatus consisting of a dry, porous substrate having two sections, communicating with one another in a moist state by capillary action, wherein a first section has a marked detection reagent for nicotine and cotinine and a second section has an immobilized binder reagent for nicotine and cotinine, and wherein the reaction product comprising nicotine and cotinine and the marked detection reagent migrates by capillary action from the first section into the second section in the moist state, wherein the marked detection reagent is a dye-carrying reagent for nicotine or cotinine, and wherein a control section, for detecting error-free performance of the test, adjoins the second section.

10. The immunoassay apparatus of claim 9, wherein in the control section, a conversion of a marked antigen or antibody or of an aqueous substrate into a colored reaction product takes place.

\* \* \* \* \*

UNITED STATES PATENT AND TRADEMARK OFFICE
CERTIFICATE OF CORRECTION

PATENT NO.    : 6,716,639 B1
DATED         : April 6, 2004
INVENTOR(S)   : Engel It is certified that error appears in the above-identified patent and that said Letters Patent is hereby corrected as shown below:

Title page,
Item [54], title should read as follows:
-- [54]  IMMUNOASSAY APPARATUS FOR DETECTING NICOTINE OR COTININE --

Signed and Sealed this

Seventeenth Day of August, 2004

JON W. DUDAS
*Acting Director of the United States Patent and Trademark Office*